United States Patent
Nöcker et al.

(10) Patent No.: US 11,013,674 B2
(45) Date of Patent: May 25, 2021

(54) HAIR TREATMENT PROCESS

(71) Applicant: KAO GERMANY GMBH, Darmstadt (DE)

(72) Inventors: Bernd Nöcker, Darmstadt (DE); Sabine Schlinkert, Darmstadt (DE); Frank Golinski, Darmstadt (DE)

(73) Assignee: KAO GERMANY GMBH, Darmstadt (DE)

(*) Notice: Subject to any disclaimer, the term of this patent is extended or adjusted under 35 U.S.C. 154(b) by 925 days.

(21) Appl. No.: 15/537,629

(22) PCT Filed: Dec. 11, 2015

(86) PCT No.: PCT/EP2015/079361
§ 371 (c)(1),
(2) Date: Jun. 19, 2017

(87) PCT Pub. No.: WO2016/102206
PCT Pub. Date: Jun. 30, 2016

(65) Prior Publication Data
US 2018/0036215 A1    Feb. 8, 2018

(30) Foreign Application Priority Data
Dec. 22, 2014  (EP) .................. 14199845

(51) Int. Cl.
| A61Q 5/04 | (2006.01) |
| A61Q 5/06 | (2006.01) |
| A61Q 5/12 | (2006.01) |
| A61K 8/36 | (2006.01) |
| A61K 8/365 | (2006.01) |
| A45D 7/06 | (2006.01) |
| A61K 8/19 | (2006.01) |
| A61K 8/34 | (2006.01) |
| A61K 8/41 | (2006.01) |
| A61K 8/898 | (2006.01) |
| A45D 2/00 | (2006.01) |

(52) U.S. Cl.
CPC ............ A61K 8/36 (2013.01); A45D 7/06 (2013.01); A61K 8/19 (2013.01); A61K 8/342 (2013.01); A61K 8/365 (2013.01); A61K 8/416 (2013.01); A61K 8/898 (2013.01); A61Q 5/04 (2013.01); A61Q 5/06 (2013.01); A61Q 5/12 (2013.01); A45D 2/001 (2013.01); A61K 2800/80 (2013.01); A61K 2800/88 (2013.01)

(58) Field of Classification Search
None
See application file for complete search history.

(56) References Cited

U.S. PATENT DOCUMENTS

| 8,906,352 B2 | 12/2014 | Malle et al. | |
| 2010/0300472 A1 | 12/2010 | Malle et al. | |
| 2013/0298933 A1 | 11/2013 | Malle et al. | |
| 2015/0305469 A1* | 10/2015 | Paul ...................... | A61K 8/342 |
| | | | 132/206 |
| 2017/0035175 A1 | 2/2017 | Malle et al. | |

FOREIGN PATENT DOCUMENTS

| EP | 2 029 236 A1 | 3/2009 | |
| WO | 2007/135299 A1 | 11/2007 | |
| WO | 2011/104282 A2 | 9/2011 | |
| WO | WO-2014072645 A1 * | 5/2014 | ............. A61K 8/731 |
| WO | WO-2015036052 A1 * | 3/2015 | ............. A61K 8/731 |

OTHER PUBLICATIONS

International Search Report dated, Feb. 4, 2016, mailed Feb. 15, 2016.

* cited by examiner

Primary Examiner — Jyothsna A Venkat
(74) Attorney, Agent, or Firm — Norris McLaughlin, P.A.

(57) ABSTRACT

The present invention relates to a process for straightening and frizz reduction of hair which leaves hair in one part straight and volumeless and the remaining part may still have the curly appearance but not frizzy at all. It has been found out when treating hair at the parts where the straight appearance is preferred with a composition comprising higher concentration of hair straightening ingredient and straightening the said part with an iron at relatively higher temperature and treating the remaining parts with a composition comprising the same straightening ingredient at a lower concentration and treating the said parts with an iron at relatively lower temperature provides hair structures which appear to be straight and with low volume in one part which is the part closer to the scalp and, curly and voluminous but not frizzy at the remaining parts which is usually the lengths.

12 Claims, No Drawings

HAIR TREATMENT PROCESS

This application is the U.S. National Stage of International Application No. PCT/EP2015/079361, filed Dec. 11, 2015, which claims foreign priority benefit under 35 U.S.C. § 119 of European Application No. 14199845.0 filed Dec. 22, 2014.

The present invention relates to a process for straightening and frizz reduction of hair which leaves hair in one part straight and volumeless and the remaining part may still have the curly appearance but not frizzy at all.

Recently hairs straightening processes and compositions designed therefore have been widely used. Their composition vary from formaldehyde, which is definitively banned in the most parts of the world because of being toxic, to alpha keto acids and most popularly to glyoxylic acid which is judged to be safe and produces satisfactory straightening effect. The processes so far established on the market involves application of the straightening composition to the whole head hair and after drying the hair, mostly without rinsing off the composition, treating the hair with an iron. Such processes deliver straight hair in the whole length of hair which results in hair without any volume and also any natural movement at all. Consumers wearing longer hair styles than shoulder length often has problem as they wish to have their hair straight at the close vicinity of the scalp but the hair should have certain level of natural curly appearance without being frizzy at the length of the hair so that it may have its natural movement.

WO 2011/104282A1 discloses semi-permanent hair straightening process of hair which involves application of glyoxylic acid, an alpha keto acid, comprising composition to the hair which is then treated with a flat iron at temperature of 180±50° C.

EP 2029236 A1 discloses hair straightening process involving application of a composition comprising pyruvic acid, lactic acid or alike onto hair and afterwards treating hair with a flat iron at a temperature of 180±50° C.

There is no process disclosed in the prior art providing a possibility to obtain hair partly straighten and partly remained curly without being frizzy. There is a great necessity to provide new hair treatment methods fulfilling consumer needs.

Inventors of the present invention have found out when treating hair at the parts where the straight appearance is preferred with a composition comprising higher concentration of hair straightening ingredient and straightening the said part with an iron at relatively higher temperature and treating the remaining parts with a composition comprising the same straightening ingredient at a lower concentration and treating the said parts with an iron at relatively lower temperature provides hair structures which appear to be straight and with low volume in one part which is the part closer to the scalp and, curly and voluminous but not frizzy at the remaining parts which is usually the lengths.

Accordingly, the first object of the present invention is a process for treating hair comprising the following steps a—30 to 90% of the hair length calculated to its total length from the scalp is applied an aqueous composition comprising at least one carboxylic acid and/or a hydrate thereof and/or a salt thereof according to the general structure

R—CO—COOH    (Formula I)

wherein R is selected from hydrogen, COOH, CN, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{10}$ cycloalkyl, optionally substituted $C_6$-$C_{10}$ aryl or a 5-10-membered, optionally substituted heteroaryl group, wherein the optional substituents of the alkyl group are selected from halogen, hydroxyl, amino and $C_1$-$C_4$ alkoxy, and the optional substituents of the other groups are selected from halogen, hydroxyl, amino, $C_1$-$C_4$ alkyl and $C_1$-$C_4$ alkoxy, at a concentration of $C_1$, b—10 to 70% of the hair length calculated to its total length from the tip of the hair is applied an aqueous composition comprising a compound according to above general structure at a concentration of $C_2$, c—leaving the compositions on the hair for 1 to 120 min d—optionally rinsing off the hair, e—drying the hair, f—treating the hair of step "a" with an iron having a surface temperature of 190 to 230° C., and g—treating the hair of step "b" with an iron having a surface temperature of 150 to 190° C., preferably 160 to 185° C., more preferably 165 to 180° C.

h—optionally rinsing off, i—optionally shampooing, and j—optionally drying the hair, with the condition that $C_1$ is larger than $C_2$ and the $C_2$ is not more than 50%, by weight, of the $C_1$, calculated to the total of the compositions.

Further object of the present invention is the use of the two compositions for straightening and frizz reduction of hair in the same treatment process.

Another object of the present invention is a kit for treating hair comprising the two compositions referred to in the above process and optionally an additional hair appliance and/or a hair treatment tool, preferably a hair iron.

In the present invention hair is divided into two parts and treated with two different aqueous compositions comprising a carboxylic acid of the above general structure. The division is made in the length of the hair starting from the root of hair fiber connected to the scalp and the percentage in length is calculated by measuring the whole length of the hair and calculating the referred percentage of the whole length either from the root or from the tip of the hair. For example, assuming that the total hair length is 30 cm and the part receiving the treatment of step "a" is set at 30 to 90% meaning that minimum of 9 cm to a maximum of 27 cm of the hair measured form the root of the hair (close to the scalp) and the part receiving the step "b" treatment is set at 10 to 70% meaning that minimum of 3 cm and maximum of 21 cm measured from the tip of the hair.

The two compositions comprise at least one carboxylic acid of the above given general structure. The suitable examples are glyoxylic acid, pyruvic acid and 2-ketobutyric acid. The most preferred is glyoxylic acid.

The carboxylic acid of the above general structure may be comprised in the composition in its free acid form. The carbonyl group adjacent to the acid group of the acid may also be present in the hydrate form. Apart from the free acid form and the hydrate thereof, salts of the acid or the hydrate may also be used.

The hydrate of the acid may be formed the acid is dissolved in an aqueous medium. For instance, glyoxylic acid (H—CO—COOH) in aqueous solution is almost quantitatively present as the hydrate (H—C(OH)$_2$—COOH). Besides, the hydrate may also condense to dimers.

A salt of the carboxylic acid of Formula (I) may also be used. As examples, alkali metal salts such as the sodium or potassium salt, alkaline earth metal salts such as the magnesium salt or the calcium salt and ammonium salts may be mentioned.

In the present invention, glyoxylic acid is the most preferred carboxylic acid of Formula (I).

The concentration $C_1$ of at least one carboxylic acid in the composition is in the range of 7.5 to 20%, preferably 7.5 to 15%, more preferably 8 to 12.5 and most preferably 8 to 10% by weight, calculated to the total of the composition, and the concentration $C_2$ in the compositions referred to in step b of the process may not exceed 50%, preferably in the range of 10 to 40%, more preferably 15 to 30% and most preferably 20 to 30% of the concentrations referred to in this paragraph for the composition used in step a of the inventive process.

The pH of the both treatment compositions is usually below or equal to 4.0, preferably in the range of 0.5 to 3.5, more preferably 1.5 to 3, most preferably 1.8 to 2.5 as measured directly and at ambient temperature (20° C.). The pH of the composition may be adjusted using alkaline solutions, preferably with sodium hydroxide solution.

The two compositions comprising the carboxylic acid are aqueous compositions and may be in the form of a solution, emulsion, cream, gel and mousse.

Both treatment compositions may also comprise auxiliary compounds such as surfactants, conditioning components, gelling agents and thickening agents.

Conventional hair shaping/straightening techniques are based on the re-organization of the disulfide bridges and involve a cleavage of the disulfide bonds by using a sulfur-based reducing agent, followed by the shaping of the hair and the formation of new disulfide bonds by the action of an oxidizing agent. In contrast, the present invention does not utilize cleavage of the disulfide bonds and fixing the bonds in the new shape. Therefore, the treatment composition of the present invention does not require the presence of sulfur-based reducing agents. The concentration of any sulfur based reducing agents should not exceed 2% by weight, calculated to total of each composition; preferably the compositions are free of sulfur based reducing agents.

The compositions may comprise one or more surfactants. As the surfactant, any of a cationic surfactant, a nonionic surfactant, an amphoteric surfactant and an anionic surfactant can be used. It is also possible to use two or more types of surfactants in combination.

The cationic surfactant is preferably a mono-long chain alkyl quaternary ammonium salt, having a $C_8$-$C_{24}$ alkyl residue and three $C_1$-$C_4$ alkyl residues.

Preferably at least one mono alkyl quaternary ammonium surfactant is selected from the compounds with the general formula

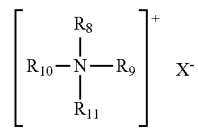

wherein $R_8$ is a saturated or unsaturated, branched or straight alkyl chain with 8-22 C atoms or

wherein $R_{12}$ is a saturated or unsaturated, branched or straight alkyl chain with 7-21 C atoms and n is an integer of 1-4, or

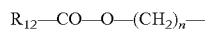

wherein $R_{12}$ is a saturated or unsaturated, branched or straight alkyl chain with 7-21 C atoms and n is an integer of 1-4, and $R_9$, $R_{10}$ and $R_{11}$ are independent from each other an alkyl group with 1 to 4 carbon atoms, hydroxyl alky chain with 1 to 4 carbon atoms, or ethoxy or propoxy group with a number of ethoxy or propoxy groups varying in the range of 1 to 4, and X is chloride, bromide, methosulfate or ethosulfate.

Suitable cationic surfactants are, for example, long-chain quaternary ammonium compounds which can be used alone or in admixture with one another, such as cetyl trimethyl ammonium chloride, myristyl trimethyl ammonium chloride, behentrimonium chloride, trimethyl cetyl ammonium bromide, stearyl trimethyl ammonium chloride, stearyl trimonium chloride and stearamidopropyltrimonium chloride.

Suitable nonionic surfactants are ethoxylated fatty alcohols according to the following formula:

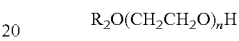

where $R_2$ is a saturated or unsaturated, linear or branched alkyl chain with 12 to 22 C atoms and n is a number between 2 and 50 preferably 2 to 40, more preferably 2 to 30. In one of the preferred embodiments of the invention, the hair treatment compositions comprise a mixture of two nonionic fatty alcohol ethoxylates, one has between 2 to 10 ethoxylate units and the other is more than 10. Those surfactants are known by the generic terms for example "Laureth", "Myristeth", "Oleth", "Ceteth", "Deceth", "Steareth" and "Ceteareth" according to the CTFA nomenclature, including addition of the number of ethylene oxide molecules. e.g. Ceteareth-20, Steareth-2.

Further nonionic surfactants suitable are those polyethylene glycol ethers of monogylcerides such as PEG-7-glyceryl cocoate known with the trade name Cetiol HE from Cognis, PEG-8-glyceryl laurate know with the trade name Glycerox L8 from Croda Chemicals, PEG-10 glyceryl oleate, PEG-15 glycerryl isostearate, PEG-5 glycerryl stearate, PEG-15 gylceryl ricinoleate, etc.

Further nonionic surfactants suitable are alkyl polyglucosides of the general formula

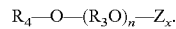

wherein $R_4$ is an alkyl group with 8 to 18 carbon atoms, $R_3$ is an ethylene or propylene group, Z is a saccharide group with 5 to 6 carbon atoms, n is a number from 0 to 10 and x is a number between 1 and 5.

Additionally useful nonionic surfactants are the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Still further suitable nonionic surfactants are amineoxides. Such amineoxides are known especially because of their use in cleansing compositions, for example $C_{12}$-$C_{18}$-alkyl dimethyl amineoxides such as lauryl dimethyl amineoxide, $C_{12}$-$C_{18}$-alkyl amidopropyl or -ethyl amineoxides, $C_{12}$-$C_{18}$-alkyl di(hydroxyethyl) or (hydroxypropyl) amineoxides, or also amineoxides with ethyleneoxide and/or propyleneoxide groups in the alkyl chain, Those are on the market, for example, under the trade names "Ammonyx®", "Aromox®" or "Genaminox®".

Anionic surfactants of the sulfate, sulfonate, carboxylate types are as well suitable in compositions of the present invention. Those are the ones very commonly used in cosmetic cleansing preparations, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof.

Additional anionic surfactants are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

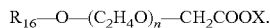

wherein $R_{16}$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids have been known for some time and are on the market, for example, under the trade name "AKYPO®" and "AKYPO-SOFT®".

Also useful are $C_8$-$C_{20}$-acyl isethionates, alone or in mixture with other anionic surfactants, as well as sulfofatty acids and the esters thereof.

It is also possible to use mixtures of several anionic surfactants in mixture within the scope of the invention.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

As further surfactant component, one or more of aqueous compositions may comprise amphoteric or zwitterionic surfactants.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

The surfactant may be comprised in the compositions singly or in combination of two or more kinds. Concentration of one or more surfactants is in the range of 0.05 to 10%, preferably 0.1 to 7.5%, more preferably 0.2 to 5%, most preferably 0.25 to 5% by weight calculated to the total of the composition.

The treatment composition may comprise one or more hair conditioning compound. Conditioners may be comprised in the compositions at a concentration in the range of 0.01 to 15%, preferably 0.05 to 10%, and more preferably 0.1% to 5% by weight calculated to the total of the composition.

Examples of the conditioning component generally include cationic polymers, silicones, fatty alcohols, and conditioning oils (for example, hydrocarbon oil, polyolefin and fatty acid ester). The composition may comprise a single type of conditioning component, or two or more in combination.

Suitable cationic polymers are copolymer of a diallyl quaternary ammonium salt include dimethyldiallylammonium chloride polymer (polyquaternium-6, for example, MERQUAT 100; Nalco Company), dimethyldiallylammonium chloride/acrylic acid copolymer (polyquaternium-22, for example, MERQUAT 280, MERQUAT 295; Nalco Company), and dimethyldiallylammonium chloride/acrylic acid amide copolymer (polyquaternium-7, for example, MERQUAT 550; Nalco Company).

Specific examples of the quaternized polyvinylpyrrolidone include quaternary ammonium salts synthesized from a copolymer of vinylpyrrolidone (VP) and dimethylaminoethyl methacrylate, and diethyl sulfate (polyquaternium 11, for example, GAFQUAT 734, GAFQUAT 755 and GAFQUAT 755N (all by ISP Japan, Ltd.)).

Specific examples of the cationized cellulose include a polymer of a quaternary ammonium salt obtained by adding glycidyltrimethylammonium chloride to hydroxyethylcellulose (polyquaternium-10, for example, RHEOGUARD G and RHEOGUARD GP (all by Lion Corp.), POLYMER JR-125, POLYMER JR-400, POLYMER JR-30M, POLYMER LR-400 and POLYMER LR-30M (all by Amerchol Corp.)), and a hydroxyethylcellulose/dimethyldiallylammonium chloride copolymer (polyquaternium-4, for example, CELQUAT H-100, CELQUAT L-200 (all by National Starch and Chemical Company)).

Cationic polymers may be comprised in the compositions at a concentration in the range of 0.01 to 5%, preferably 0.05 to 4%, and more preferably 0.1% to 2.5% by weight calculated to the total of the composition.

In order to improve the feel of use, the treatment composition preferably comprises one or more silicone. Examples of the silicone include dimethylpolysiloxane, and modified silicone (for example, amino-modified silicone, fluorine-modified silicone, alcohol-modified silicone, polyether-modified silicone, epoxy-modified silicone, or alkyl-modified silicone), but dimethylpolysiloxane, polyether-modified silicone and amino-modified silicone are preferred.

The dimethylpolysiloxane may be any cyclic or non-cyclic dimethylsiloxane polymer, and examples thereof include SH200 series, BY22-019, BY22-020, BY11-026, B22-029, BY22-034, BY22-050A, BY22-055, BY22-060, BY22-083, FZ-4188 (all by Dow Corning Toray Co., Ltd.), KF-9008, KM-900 series, MK-15H, and MK-88 (all by Shin-Etsu Chemical Co., Ltd.).

The polyether-modified silicone may be any silicone having a polyoxyalkylene group, and the group constituting the polyoxyalkylene group may be an oxyethylene group or an oxypropylene group. More specific examples include KF-6015, KF-945A, KF-6005, KF-6009, KF-6013, KF-6019, KF-6029, KF-6017, KF-6043, KF-353A, KF-354A, KF-355A (all by Shin-Etsu Chemical Co., Ltd.), FZ-2404, SS-2805, FZ-2411, FZ-2412, SH3771M, SH3772M, SH3773M, SH3775M, SH3749, SS-280X series, BY22-008 M, BY11-030, and BY25-337 (all by Dow Corning Toray Co., Ltd.).

The amino-modified silicone may be any silicone having an amino group or an ammonium group, and examples thereof include an amino-modified silicone oil having all or a part of the terminal hydroxyl groups capped with a methyl group or the like, and an amodimethicone which does not have the terminals capped. A preferred example of the amino-modified silicone may be a compound represented by the following formula:

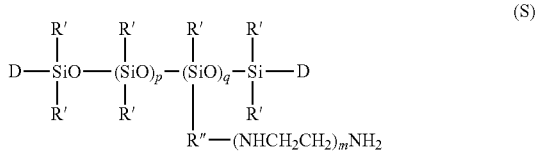

(S)

wherein R' represents a hydroxyl group, a hydrogen atom or $R^X$; $R^X$ represents a substituted or unsubstituted monovalent hydrocarbon group having 1 to 20 carbon atoms; D represents $R^X$, $R''—(NHCH_2CH_2)_mNH_2$, $OR^X$, or a hydroxyl group; R" represents a divalent hydrocarbon group having 1 to 8 carbon atoms; m represents a number from 0 to 3; p and q represent numbers, the sum of which is, as a number average, equal to or greater than 10 and less than 20,000, preferably equal to or greater than 20 and less than 3000, more preferably equal to or greater than 30 and less than 1000, and even more preferably equal to or greater than 40 and less than 800.

Specific examples of suitable commercially available products of the amino-modified silicone include amino-modified silicone oils such as SF8452C, SS-3551 (all by Dow Corning Toray Co., Ltd.), KF-8004, KF-867S, and KF-8015 (all by Shin-Etsu Chemical Co., Ltd.); and amodimethicone emulsions such as SM8704C, SM8904, BY22-079, FZ-4671, and FZ-4672 (all by Dow corning Toray Co., Ltd.).

The total content of these silicones in the treatment composition of the present invention is usually 0.1 to 10%, preferably 0.2% to 7.5% and more preferably 0.5 to 5%, by weight calculated to the total of the composition.

For improving the feel upon use, the treatment composition may also include an organic conditioning oil. Suitable ones are selected from a hydrocarbon oil having at least 10 carbon atoms, a polyolefin, a fatty acid ester, a fatty acid amide and mixtures thereof.

Examples of the hydrocarbon oil include a cyclic hydrocarbon, a linear aliphatic hydrocarbon (saturated or unsaturated), and a branched aliphatic hydrocarbon (saturated or unsaturated), and polymers or mixtures thereof are also included. The linear hydrocarbon oil preferably has 12 to 19 carbon atoms. The branched hydrocarbon oil includes hydrocarbon polymers, and preferably has more than 19 carbon atoms.

The polyolefin is a liquid polyolefin, more preferably a liquid poly-α-olefin, and even more preferably a hydrogenated liquid poly-α-olefin. The polyolefin used herein is prepared by polymerizing an olefin monomer having 4 to 14 carbon atoms, and preferably 6 to 12 carbon atoms.

The fatty acid ester may be, for example, a fatty acid ester having at least 10 carbon atoms. Examples of such a fatty acid ester include esters having a hydrocarbon chain derived from a fatty acid and an alcohol (for example, monoesters, polyhydric alcohol esters, or di- and tricarboxylic acid esters). The hydrocarbon group of these fatty acid esters may have another compatible functional group such as an amide group or an alkoxy group as a substituent, or the hydrocarbon group may be covalently bonded to those functional groups. More specifically, an alkyl and alkenyl ester of a fatty acid having a fatty acid chain having 10 to 22 carbon atoms, a carboxylic acid ester of an aliphatic alcohol having an aliphatic chain derived from an alkyl and/or alkenyl alcohol having 10 to 22 carbon atoms, and a mixture thereof are suitably used. Specific examples of these preferred fatty acid esters include isopropyl isostearate, hexyl laurate, iso-hexyl laurate, isohexyl palmitate, isopropyl palmitate, decyl oleate, isodecyl oleate, hexadecyl stearate, decyl stearate, dihexadecyl adipate, lauryl lactate, myristyl lactate, cetyl lactate, oleyl stearate, oleyl oleate, oleyl myristate, lauryl acetate, cetyl propionate and dioleyl adipate.

Further suitable oil components are natural oils such as paraffin oil and natural triglycerides.

Suitable natural triglycerides are argan oil, shea butter oil, karite oil, olive oil, almond oil, avocado oil, ricinus oil, coconut oil, palm oil, sesame oil, peanut oil, sunflower oil, peach kernel oil, wheat germ oil, macadamia nut oil, macadamia oil, night primrose oil, jojoba oil, castor oil, soya oil, lanolin, passiflora oil, black cumin oil, borage oils, grapeseed oil, hempseed oil, kukui nut oil, and rosehip oil.

The organic conditioning oil may be used in combination of two or more kinds, and the total concentration is typically in the range of 0.1 to 10%, preferably 0.2% to 7.5% and more preferably 0.5 to 5%, by weight calculated to the total of the composition.

The compositions may also contain a fatty alcohol having 8 carbon atoms or more. Usually, the higher alcohol has 8 to 22 carbon atoms, and preferably 16 to 22 carbon atoms. Specific examples thereof include cetyl alcohol, stearyl alcohol, behenyl alcohol, and mixtures thereof.

The fatty alcohol may be used in combination of two or more kinds, and the content thereof is typically 0.1 to 10%, preferably 0.2% to 7.5% and more preferably 0.5 to 5%, by weight calculated to the total of the composition.

Additionally polyols may suitably be comprised in the compositions. Suitable ones are panthenol, glycerin, glycol and derivatives, polyethyleneglycoles known with trade names Carbowax PEG from Union Carbide and Polyox WSR range from Amerchol, polyglycerin, polyethyleneglycol mono or di fatty acid esters.

Compositions may comprise other compounds found conventionally in cosmetic compositions such as fragrances, preservatives etc.

Following examples are to illustrate the invention but not to limit it.

EXAMPLE 1

Composition 1

|  | % by weight |
|---|---|
| Glyoxylic acid | 10.0 |
| Amodimethicone | 1.2 |
| Cetearyl alcohol | 3.5 |
| Cetrimonium chloride | 1.0 |
| Fragrance | 1.0 |
| Sodium hydroxide | to pH 2.0 |
| Water | to 100 |

Composition 2

|  | % by weight |
|---|---|
| Glyoxylic acid | 3.0 |
| Amodimethicone | 0.8 |
| Cetrimonium chloride | 1.0 |
| Fragrance | 0.7 |
| Sodium hydroxide | to pH 2.0 |
| Water | to 100 |

C2 (3.0% by weight) is 30% of the C1 (10.0% by weight).

With the above two compositions hair of a volunteer having a length of 35 cm was treated. The hair was washed first with a commercially available cleansing shampoo composition and towel dried. The first composition was then applied onto the 14 cm (40%) of the hair measured from the scalp and the composition 2 was applied to the remaining 21 cm (60%) of the hair and the compositions were left on the hair for 20 min and the hair was dried afterwards. Afterwards, the part treated with the composition 1, the first 14 cm, was treated with an iron having a surface temperature of 220° C. and the part treated with the composition 2, the lower 21 cm, was treated with an iron having a surface temperature of 170° C.

It was observed that the upper part of the hair was well straightened and had almost no volume whereas the lower part appeared to be still curly with big curls, although less curly than prior to the treatment, and had no frizzy appearance and had volume and the hair had natural movements with the head movements.

Treating whole hair either with only composition 1 or only with composition 2 did not allow to obtain the above result. Treating hair only with composition 1 delivered straight hair with no curls at all and hair had lost its complete volume. On the other hand, treating whole hair with composition 2 did not provide hair parts enough straightening which was the aim of the treatment.

EXAMPLE 2

Composition 1

| | % by weight |
|---|---|
| Glyoxylic acid | 9.0 |
| Amodimethicone | 1.0 |
| Behentrimonium chloride | 0.8 |
| Fragrance | 1.0 |
| Sodium hydroxide | to pH 2.0 |
| Water | to 100 |

Composition 2

| | % by weight |
|---|---|
| Glyoxylic acid | 1.8 |
| Amodimethicone | 0.8 |
| Steartrimonium chloride | 0.6 |
| Fragrance | 0.7 |
| Sodium hydroxide | to pH 2.0 |
| Water | to 100 |

C2 (1.8.0% by weight) is 20% of the C1 (9.0% by weight).

Similar results were obtained as in the Example 1.

EXAMPLE 3

Composition 1

| | % by weight |
|---|---|
| Glyoxylic acid | 10.0 |
| Amodimethicone | 1.0 |
| Behentrimonium chloride | 0.8 |
| Hydroxyethylcellulose | 1.0 |
| Fragrance | 1.0 |

| | % by weight |
|---|---|
| Sodium hydroxide | to pH 2.0 |
| Water | to 100 |

Composition 2

| | % by weight |
|---|---|
| Glyoxylic acid | 2.5 |
| Amodimethicone | 0.8 |
| Steartrimonium chloride | 0.6 |
| Xanthan gum | 0.5 |
| Fragrance | 0.7 |
| Sodium hydroxide | to pH 2.0 |
| Water | to 100 |

C2 (2.5% by weight) is 25% of the C1 (10.0% by weight).

Similar results were obtained as in the Example 1.

The invention claimed is:

1. A process for treating hair comprising:
   a) applying, to 30 to 60% of a first hair length calculated to its total length from the scalp, a first aqueous composition comprising
   b) applying, to 40 to 70% of a second hair length calculated to its total length from the tip of the hair, a second aqueous composition comprising at a concentration of C2;
   c) leaving the first and second aqueous compositions on the hair for 1 to 120 min;
   d) optionally rinsing the first and second aqueous compositions off the hair;
   e) drying the hair;
   f) treating the first hair length of a) with an iron having a first surface temperature of 190 to 230° C.;
   g) treating the second hair length of b) with an iron having a second surface temperature of 150 to 190° C.;
   h) optionally rinsing the first and second aqueous compositions off the hair;
   i) optionally shampooing the hair; and
   j) optionally drying the hair,
   wherein
      C1 is larger than C2, and
      the C2 is not more than 50%, by weight of the C1, calculated to a total of the first and second aqueous compositions.

2. The process of claim 1, wherein the aqueous compositions of a) and b) have a pH of 4.0 or lower.

3. The process of claim 1, wherein the aqueous compositions of a) and b) do not comprise more than 2% by weight, calculated to the total of each aqueous composition, any sulfur based reducing agent.

4. The process of claim 1, wherein the aqueous compositions of a) and b) comprise one or more surfactants selected from cationic, anionic, nonionic, and amphoteric surfactants.

5. The process of claim 1, wherein the aqueous compositions of a) and b) comprise at least one mono alkyl quaternary ammonium surfactant selected from compounds with the general formula

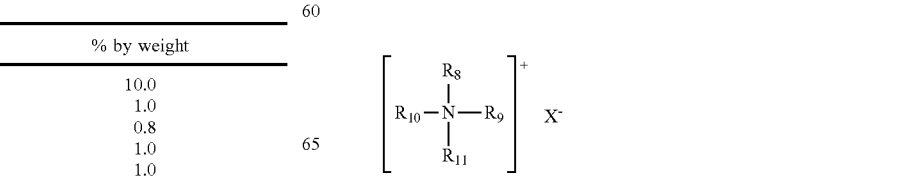

wherein $R_8$ is a saturated or unsaturated, branched or straight alkyl chain with 8-22 carbon atoms or

$$R_{12}-CO-NH-(CH_2)_n-$$

wherein $R_{12}$ is a saturated or unsaturated, branched or straight alkyl chain with 7-21 carbon atoms and n is an integer of 1-4, or

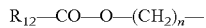
$$R_{12}-CO-O-(CH_2)_n-$$

wherein $R_{12}$ is a saturated or unsaturated, branched or straight alkyl chain with 7-21 carbon atoms and n is an integer of 1-4, and $R_9$, $R_{10}$ and $R_{11}$ are independent from each other an alkyl group with 1 to 4 carbon atoms, hydroxyl alky chain with 1 to 4 carbon atoms, or ethoxy or propoxy group with a number of ethoxy or propoxy groups varying in the range of 1 to 4, and X is chloride, bromide, methosulfate or ethosulfate.

6. The process of claim 1, wherein the aqueous compositions of a) and b) comprise one or more surfactants selected from cationic, anionic, nonionic, and amphoteric surfactants, at a concentration in the range of 0.05 to 10% by weight calculated to the total of the aqueous composition.

7. The process of claim 1, wherein the aqueous compositions of a) and b) comprise one or more hair conditioning compound.

8. The process of claim 1, wherein the aqueous compositions of a) and b) comprise at least one hair conditioning compound selected from cationic polymers, silicones, fatty alcohols, and conditioning oils, at a total concentration in the range of 0.01 to 15% by weight calculated to the total aqueous composition.

9. The process of claim 1, wherein the aqueous compositions of a) and b) comprise one or more silicone, at a concentration in the range of 0.1 to 10% by weight, calculated to the total of the aqueous composition.

10. The process of claim 1, wherein the aqueous compositions of a) and b) comprise aminated silicone.

11. The process of claim 1, wherein the aqueous compositions of a) and b) comprise one or more fatty alcohols, at a concentration in the range of 0.1 to 10% by weight, calculated to the total of the aqueous composition.

12. The process of claim 1, wherein the first surface temperature is greater than the second surface temperature.

* * * * *